US010577165B2

(12) United States Patent
Sadowski et al.

(10) Patent No.: US 10,577,165 B2
(45) Date of Patent: Mar. 3, 2020

(54) KEY RETENTION SYSTEM FOR PRODUCT PACKAGING

(71) Applicant: SEE Forming L.L.C., Appleton, WI (US)

(72) Inventors: Scott James Sadowski, Appleton, WI (US); Mark Allan Erickson, Trevor, WI (US)

(73) Assignee: SEE Forming L.L.C., Appleton, WI (US)

( * ) Notice: Subject to any disclaimer, the term of this patent is extended or adjusted under 35 U.S.C. 154(b) by 278 days.

(21) Appl. No.: 15/714,828

(22) Filed: Sep. 25, 2017

(65) Prior Publication Data
US 2019/0092547 A1    Mar. 28, 2019

(51) Int. Cl.
A61B 50/30     (2016.01)
B65D 77/26     (2006.01)
A61B 50/00     (2016.01)
A61B 50/33     (2016.01)
A61B 50/20     (2016.01)

(52) U.S. Cl.
CPC .............. B65D 77/26 (2013.01); A61B 50/30 (2016.02); A61B 50/20 (2016.02); A61B 50/33 (2016.02); A61B 2050/0067 (2016.02); A61B 2050/0076 (2016.02); A61B 2050/0083 (2016.02)

(58) Field of Classification Search
CPC ......... A61B 50/30; A61B 50/20; A61B 50/33; A61B 2050/0067; A61B 2050/0076; A61B 2050/0083; A61M 25/002; A61M 5/002; B65D 77/26; B65D 25/10; G11B 33/0427; A45C 13/02

USPC ...... 206/438, 1.5, 349, 308, 310; 248/316.7, 248/222.12; 211/89.01, 120, 124, 69.8, 211/69.9, 85.13
See application file for complete search history.

(56) References Cited

U.S. PATENT DOCUMENTS

| 774,037 | A | * | 11/1904 | Burgi | ................. | G11B 33/0494 |
| | | | | | | 206/312 |
| 2,720,969 | A | * | 10/1955 | Kendall | ................ | A61M 5/002 |
| | | | | | | 206/365 |
| 3,933,240 | A | | 1/1976 | Humble | | |
| 3,983,996 | A | * | 10/1976 | Hendren, III | ....... | A61M 25/002 |
| | | | | | | 206/363 |
| 4,019,633 | A | * | 4/1977 | Roth | ........................ | A61F 6/14 |
| | | | | | | 206/364 |
| 4,697,703 | A | | 10/1987 | Will | | |
| 4,938,355 | A | * | 7/1990 | Rocco | .................... | B44D 3/121 |
| | | | | | | 206/372 |

(Continued)

FOREIGN PATENT DOCUMENTS

EP       2206480 A1    7/2010
WO    2015080578 A1    6/2015

Primary Examiner — Gideon R Weinerth
(74) Attorney, Agent, or Firm — Middleton Reutlinger

(57) ABSTRACT

A package for a product and method of retaining and releasing a product, where a container body is configured to support the product and includes a key support and a retaining key that is supported by the key support. The retaining key is movable between locked and released configurations, while in the locked configuration the retaining key retains a portion of the product and while in the released configuration the retaining key retracts to facilitate removal of the product from the container body.

25 Claims, 13 Drawing Sheets

(56) References Cited

U.S. PATENT DOCUMENTS

| | | | | |
|---|---|---|---|---|
| 5,386,908 A * | 2/1995 | Sinn | ............... | A61B 17/06133 |
| | | | | 206/363 |
| 5,501,341 A | 3/1996 | Van Es | | |
| 5,526,926 A * | 6/1996 | Deja | ............... | G11B 33/0427 |
| | | | | 206/308.1 |
| 5,590,768 A * | 1/1997 | Hilton | ............... | G11B 33/0422 |
| | | | | 206/308.1 |
| 5,601,189 A | 2/1997 | Roshdy | | |
| 5,772,031 A * | 6/1998 | Landis | ............... | A61B 50/30 |
| | | | | 206/363 |
| 6,047,826 A * | 4/2000 | Kalinski | ............... | A61B 17/06114 |
| | | | | 206/365 |
| 6,123,192 A * | 9/2000 | Rufo, Jr. | ............... | G11B 33/0427 |
| | | | | 206/308.1 |
| 6,164,446 A * | 12/2000 | Law | ............... | G11B 33/0422 |
| | | | | 206/308.1 |
| 6,196,388 B1 * | 3/2001 | Kaposvari | ............... | A45C 11/34 |
| | | | | 206/214 |
| 6,216,885 B1 * | 4/2001 | Guillaume | ............... | A61M 5/008 |
| | | | | 206/366 |
| D442,697 S * | 5/2001 | Hajianpour | ............... | D24/229 |
| 6,412,631 B2 * | 7/2002 | Belden, Jr. | ............... | G11B 33/0427 |
| | | | | 206/308.1 |
| 6,443,300 B1 * | 9/2002 | Gelardi | ............... | G11B 33/0427 |
| | | | | 206/1.5 |
| 6,527,115 B2 | 3/2003 | Rabiner et al. | | |
| 6,547,068 B2 * | 4/2003 | Chu | ............... | G11B 33/0427 |
| | | | | 206/308.1 |
| 6,588,587 B2 | 7/2003 | Johnson et al. | | |
| 6,839,239 B1 * | 1/2005 | Lee | ............... | H05K 5/0286 |
| | | | | 206/308 |
| 6,892,878 B2 * | 5/2005 | Hegarty | ............... | G11B 33/0427 |
| | | | | 206/308.1 |
| 6,892,881 B2 | 5/2005 | Leitch | | |
| 6,915,901 B2 * | 7/2005 | Feinberg | ............... | A61B 17/00491 |
| | | | | 206/363 |
| 6,955,068 B2 * | 10/2005 | Gelardi | ............... | E05B 73/0023 |
| | | | | 206/1.5 |
| 7,527,148 B2 * | 5/2009 | Crouan | ............... | G11B 33/0422 |
| | | | | 206/308.1 |
| 7,987,977 B2 | 8/2011 | Leedom et al. | | |
| 8,109,480 B2 * | 2/2012 | Lee | ............... | G02F 1/133608 |
| | | | | 24/456 |
| 8,657,106 B2 | 2/2014 | Trapp et al. | | |
| 8,727,117 B2 | 5/2014 | Maasarani | | |
| 9,265,578 B2 | 2/2016 | Dacey | | |
| 9,687,300 B2 | 6/2017 | Hartfelder et al. | | |
| 2002/0100701 A1 * | 8/2002 | Chiu | ............... | G11B 33/0422 |
| | | | | 206/308.1 |
| 2003/0000855 A1 * | 1/2003 | Lin | ............... | G11B 33/0427 |
| | | | | 206/310 |
| 2003/0121821 A1 * | 7/2003 | Roshdy | ............... | A61B 50/33 |
| | | | | 206/570 |
| 2004/0007482 A1 * | 1/2004 | Wen-Long | ............... | G11B 33/0427 |
| | | | | 206/308.1 |
| 2005/0098460 A1 * | 5/2005 | Smith | ............... | A61B 50/30 |
| | | | | 206/366 |
| 2007/0029216 A1 * | 2/2007 | Liu | ............... | G11B 33/0427 |
| | | | | 206/310 |
| 2011/0315565 A1 * | 12/2011 | Chiappini | ............... | F42B 39/22 |
| | | | | 206/1.5 |
| 2012/0247988 A1 * | 10/2012 | Lax | ............... | G11B 33/0427 |
| | | | | 206/308.1 |
| 2015/0224247 A1 * | 8/2015 | McDorman | ............... | A61M 5/003 |
| | | | | 206/569 |
| 2016/0206510 A1 | 7/2016 | Carrel et al. | | |
| 2016/0354151 A1 | 12/2016 | Nadig et al. | | |
| 2018/0311027 A1 * | 11/2018 | Distefano | ............... | A61B 50/20 |
| 2018/0370667 A1 * | 12/2018 | Bogdziewicz | ............... | B65B 19/226 |
| 2019/0092547 A1 * | 3/2019 | Sadowski | ............... | A61B 50/30 |

* cited by examiner

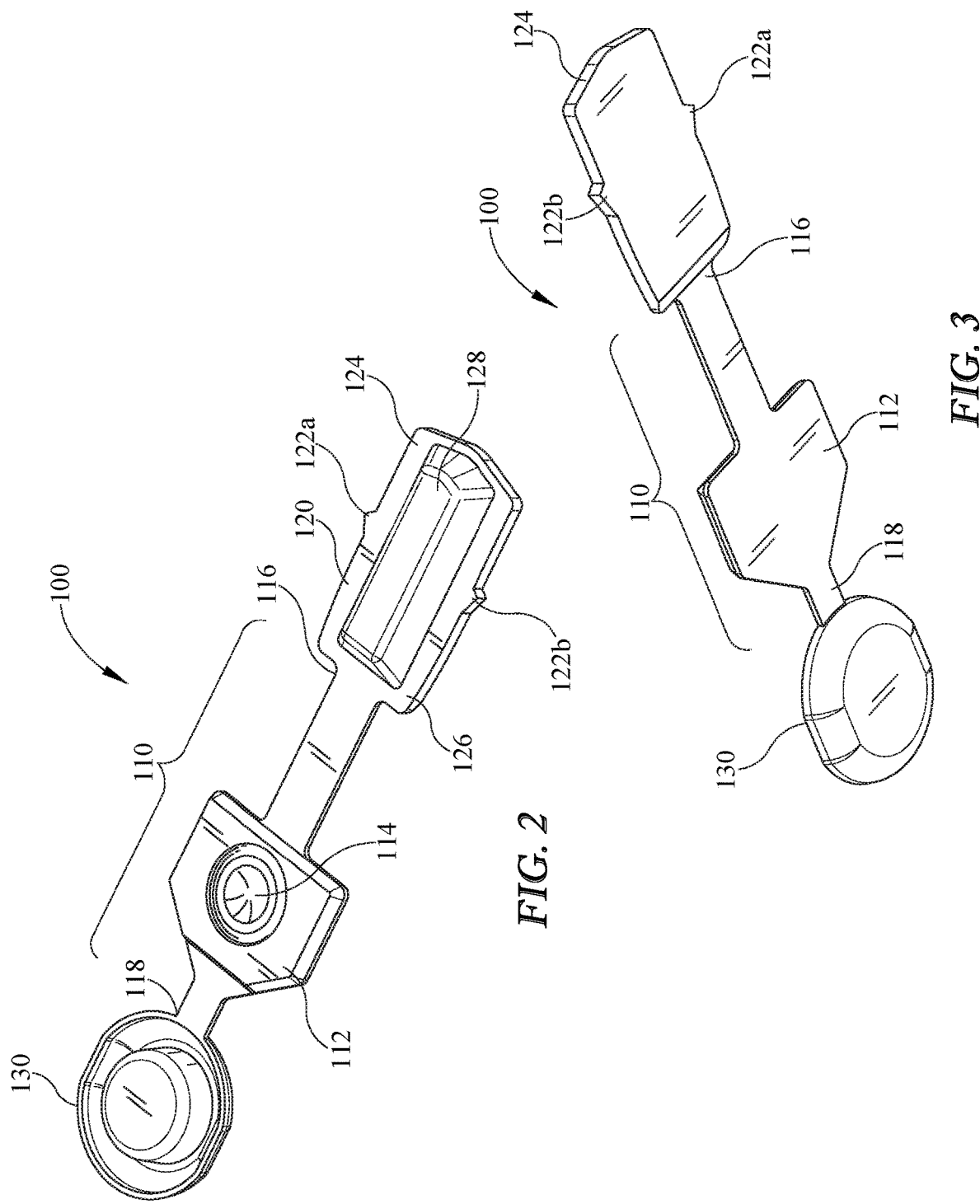

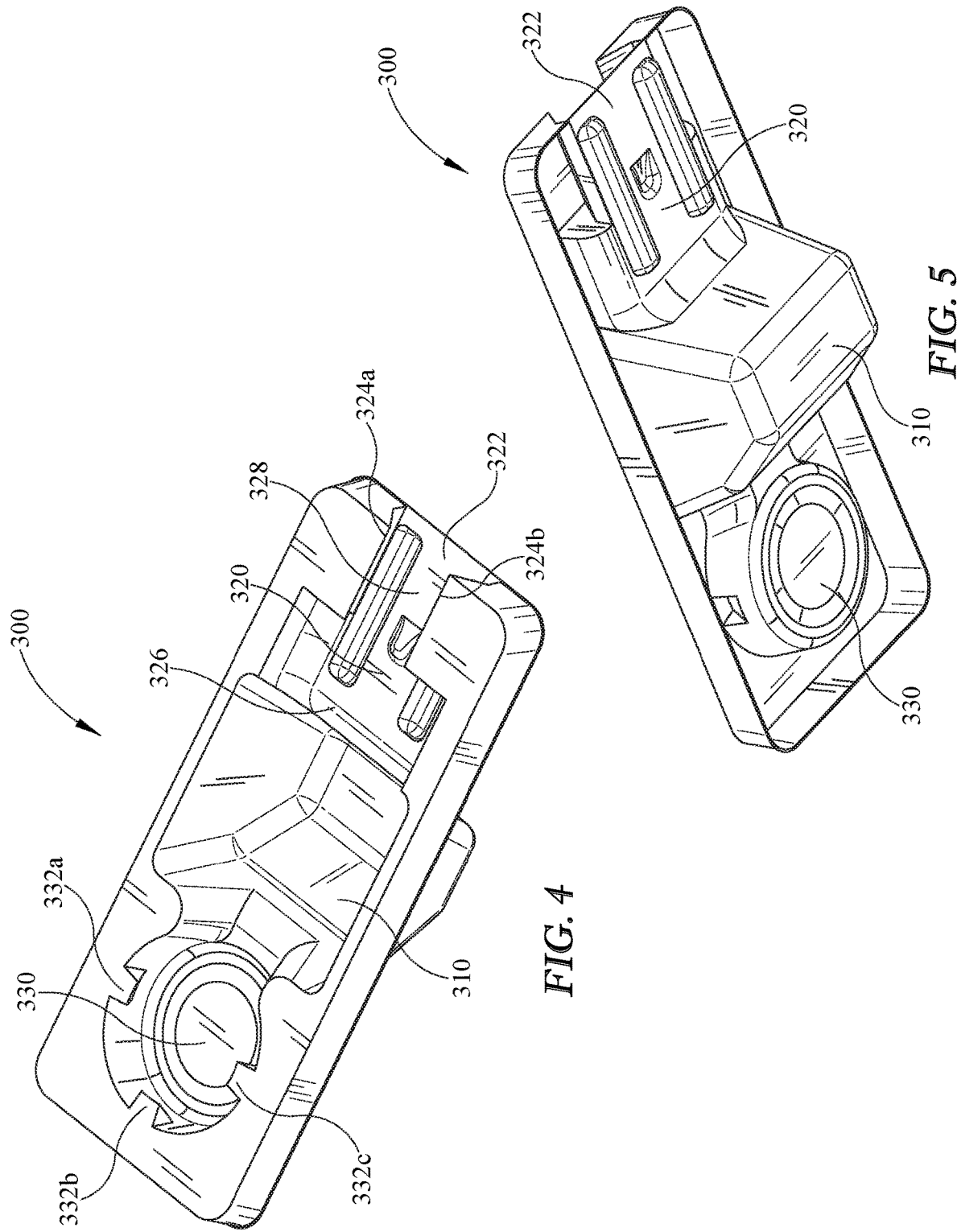

KEY RETENTION SYSTEM FOR PRODUCT PACKAGING

BACKGROUND

Conventionally, products have been packaged in a variety of ways, many of which present various limitations, including difficulty for an end user to insert the product within the package and/or to release the product without damage or loss to the contained products. An example of conventional packaging includes packaging molded or thermoformed into a rigid or semi-rigid plastic container for holding one or more products in one or more predetermined locations in the container. Another conventional type of packaging includes a flexible pouch into which product components may be inserted. In some instances these packaging techniques may be combined. Containing products within a tray, pouch, or the like may also be supplemented by additional elements such as covers, straps, adhesive tape, or the like. The use of such additional elements, however, may not be desirable and may be cumbersome to the end user.

In particular, many packaging systems are subject to the competing desires of securely retaining and protecting products within packages during shipment and otherwise prior to use, and of enabling retained products to be quickly and easily removed from the packaging when needed. With some medical equipment, for example, it may be desirable to securely retain delicate and sterilized instruments used in medical procedures within a package for shipment and storage, yet enable those instruments to be removed as quickly and effortlessly as possible during the medical procedures.

Further, environmental concerns remain an important concern in the packaging industry, so it is also desirable to minimize waste associated with packaging systems both in connection with the manufacture of packaging and its disposal and/or recycling after use.

SUMMARY

Apparatuses and methods for product packaging are disclosed herein. An example package for a product, for example, includes a container body that is configured to support the product and including a key support, and a retaining key supported by the key support and movable between locked and released configurations, where in the locked configuration the retaining key retains a portion of the product when the product is supported by the container body and in the released configuration, the retaining key retracts to facilitate removal of the product from the container body when the product is supported thereby. The retaining key includes a tab portion, a deformable portion and an anchor portion, and the deformable portion extends between the tab portion and the anchor portion and is configured to be suspended over a void defined by the key support when the retaining key is supported by the key support. The depression of the deformable portion into the void moves the retaining key from the locked configuration to the released configuration, and the tab portion is disposed proximate a first end of the deformable portion and is configured to retain the portion of the product when the product is supported by the container body and the retaining key is in the locked configuration, and the anchor portion is disposed proximate a second end of the deformable portion and is configured to anchor the retaining key to the key support proximate the second end thereof.

In some embodiments, the deformable portion includes a push target for depressing the deformable portion into the void. In other embodiments, the push target for depressing the deformable portion into the void is sized and configured to be activated by a user's finger.

In some embodiments, the key support is integrally-formed with the container body. In some embodiments, the tab portion is about ⅜ inches in length. In other embodiments, the retaining key is inseparable from the key support. In still other embodiments, the product is a medical device.

In some instances, the apparatus is a retaining key for packaging a product, including a tab portion, a deformable portion and an anchor portion; where the deformable portion extends between the tab portion and the anchor portion and is configured to be suspended over a void defined by a key support in a container body that supports the product; where the depression of the deformable portion into the void moves the retaining key from a locked configuration to a released configuration; where the tab portion is disposed proximate a first end of the deformable portion and is configured to retain a portion of the product when the product is supported by the container body and the retaining key is in the locked configuration; where the anchor portion is disposed proximate a second end of the deformable portion and is configured to anchor the retaining key to the key support proximate the second end thereof; and, where the retaining key is movable between the locked and released configurations, where in the locked configuration the retaining key retains a portion of the product when the product is supported by the container body and in the released configuration, the retaining key retracts to facilitate removal of the product from the container body when supported thereby.

In some embodiments, the deformable portion includes a push target for depressing the deformable portion into the void. In other embodiments, the push target for depressing the deformable portion into the void is sized and is configured to be activated by a user's finger. In still other embodiments, the tab portion is about ⅜ inches in length. In some embodiments, the deformable portion is narrower than the tab portion.

In some instances, the apparatus is a key support for packaging a product, including a depression void that is capable of receiving a deformable portion of a retaining key when the deformable portion is depressed into the depression void; a tab void that is capable of at least partially receiving a tab portion of the retaining key proximate a first end of the deformable portion of the retaining key; an anchor retainer that is capable of receiving an anchor portion of a retaining key proximate a second end of the deformable portion of the retaining key; where the key support supports the retaining key in a container body and allows the retaining key to move between locked and released configurations, and where in the locked configuration the retaining key retains a portion of the product when the product is supported by the container body and in the released configuration, the retaining key retracts to facilitate removal of the product from the container body when supported thereby.

In some embodiments, the key support is integrally-formed with the container body. In other embodiments, the depression void is substantially rectangular in shape. In still other embodiments, the anchor retainer is substantially circular in shape. In some embodiments, the anchor retainer includes a top portion and a bottom portion, where the top portion includes one or more tapered tabs at an angle such that the tapered tabs taper inwardly to align with the bottom portion of the anchor retainer to hold the anchor portion in place. In other embodiments, the deformable portion of the retaining key is narrower in cross-section than the tab portion of the retaining key, where the tab void includes a channel sized and is configured to receive the tab portion of the retaining key for movement along a first axis and formed from a first tapered wall and a second tapered wall, where the first and the second tapered walls are separated by a gap that is narrower than the tab portion of the retaining key but wider than at least a portion of the deformable portion of the retaining key to enable the at least a portion of the deformable portion of the retaining key to be inserted into the channel of the tab void when attaching the retaining key to the key support, and where the tab void is positioned relative to the anchor retainer such that at least a portion of the tab portion is positioned within the channel when the anchor portion of the retaining key is received by the anchor retainer of the key support.

In some instances, the apparatus is a package for a product, including a container body configured to support the product; a depression void adjacent a deformable portion of a retaining key, where the depression void receives the deformable portion when the deformable portion is depressed into the depression void; a tab void at least partially supporting a tab portion of the retaining key proximate a first end of the deformable portion of the retaining key; an anchor retainer supporting an anchor portion of the retaining key proximate a second end of the deformable portion of the retaining key; where the depression void, tab void, and anchor retainer support the retaining key and allow the retaining key to move between locked and released configurations, where in the locked configuration the retaining key retains a portion of the product when the product is supported by the container body and in the released configuration, the retaining key retracts to facilitate removal of the product from the container body when supported thereby.

In some embodiments, the depression void, tab void, and anchor retainer are integrally-formed with the container body. In other embodiments, the product is a medical device.

In some instances, the apparatus is a package for a product, including a thermoformed container body configured to support the product; a tab void at least partially supporting a tab portion of a retaining key; an anchor retainer supporting an anchor portion of the retaining key; where the tab void and anchor retainer support the retaining key and allow the retaining key to slide between locked and released configurations, where in the locked configuration the retaining key retains a portion of the product when the product is supported by the container body and in the released configuration, the retaining key retracts to facilitate removal of the product from the container body when supported thereby.

In some instances the apparatus is a mold for use in product packaging container, including a depression void portion that is capable of defining a depression void in a container body that receives a deformable portion of a retaining key when the deformable portion is depressed into the depression void; a tab void portion capable of defining a tab void in the container body that at least partially receives a tab portion of the retaining key proximate a first end of the deformable portion of the retaining key; an anchor retainer portion capable of defining an anchor retainer in the container body that receives an anchor portion of the retaining key proximate a second end of the deformable portion of the retaining key; where the depression void, tab void, and anchor retainer support form a key support when used into combination with a container body configured to support the product.

In some embodiments, the thermoform mold is substantially rectangular in shape. In other embodiments, the depression void is substantially rectangular in shape. In still other embodiments, the anchor retainer is substantially circular in shape. In some embodiments, the mold further comprises one or more articulating locks, where the one or more articulating locks are movable from a molding position to a release position and biased towards the molding position. In other embodiments, the one or more articulating locks movable horizontally and vertically from a molding position to a release position.

In some instances, the method is a method of retaining a product in a container body, including loading the product into the container body, such that the product is held in place in two dimensions by the container body; inserting a retaining key into a key support of the container body in a loading position, such that a tab portion of the retaining key is extended over the product in the loading position; and locking the retaining key into an anchored position, such that the tab portion of the retaining key is at least partially extended over the product such that movement of the product in a third dimension is restricted.

In some embodiments, locking the retaining key further includes sliding the retaining key generally along a longitudinal axis thereof into the anchored position. In other embodiments, locking the retaining key further includes rotating the key about an axis into the anchored position.

In some embodiments, the product is a medical device. In other embodiments, the key support is integrally-formed with the container body. In still other embodiments, the container body includes a plurality of key supports, where the method further includes locking a plurality of retaining keys into respective key supports among the plurality of key supports.

In some embodiments, once inserted the retaining key is inseparable from the key support.

In some instances, the method is a method of releasing a product locked into a container body by a retaining key supported by a key support, where the retaining key includes a deformable portion extending between a tab portion and an anchor portion and suspended over a void defined by the key support, where the tab portion extends over at least a portion of the product to lock the product into the container body, and where the anchor portion anchors the retaining key to the key support, the method including activating the deformable portion of the retaining key by depressing the deformable portion into a void of the key support to retract the tab portion of the retaining key away from the product and thereby move the retaining key from a locked configuration to a released configuration; and removing the product from the container body after activating the deformable portion.

In some embodiments, the deformable portion contains a push target for depressing the deformable portion into the void sized and configured to be activated by a user's finger.

In some embodiments, the product is a medical device. In other embodiments, the container body includes a plurality of key supports, and where the method further comprises activating deformable portions of a plurality of retaining keys supported by respective key supports among the plurality of key supports.

In some instances, the method is a method of releasing a product locked into a container body by a retaining key supported by a post, the method including activating an anchor portion of the retaining key by rotating the anchor portion about the post such that the retaining key moves from a locked configuration to a released configuration; and, removing the product from the container body.

In some embodiments, the anchor portion contains one or more protrusions configured to couple with one or more indentions of the post.

In some embodiments, the product is a medical device.

In some instances, the apparatus is a package for a product including a container body configured to support the product and including a key support; a retaining key supported by the key support and movable between locked and released configurations, where in the locked configuration the retaining key retains a portion of the product when the product is supported by the container body and in the released configuration, the retaining key rotates to facilitate removal of the product from the container body when the product is supported by the container, and where the retaining key includes: a cam portion configured as an eccentric disc and configured to mechanically link to the key support when the retaining key is supported by the key support, where the rotation of the cam portion moves the retaining key from the locked configuration to the released configuration and where the tab portion is configured to retain the portion of the product when the product is supported by the container body and the retaining key is in the locked configuration.

In some instances, the apparatus is a container body configured to support a product, including a product void supporting the product in two dimensions; a depression void supporting a deformable portion of a retaining key, where the depression void receives the deformable portion when the deformable portion is depressed into the depression void; a tab void at least partially supporting a tab portion of the retaining key proximate a first end of the deformable portion of the retaining key; an anchor retainer supporting an anchor portion of a retaining key proximate a second end of the deformable portion of the retaining key; and where the depression void, tab void, and anchor retainer support the retaining key and allow the retaining key to move between locked and released configurations, wherein in the locked configuration the retaining key retains a portion of the product when the product is supported by the product void and in the released configuration, the retaining key retracts to facilitate removal of the product from the product void when supported thereby.

In some instances, the apparatus is a mold for use in a thermoforming process, including a void portion capable of defining an object to be formed; and, one or more articulating locks, where each of the one or more articulating locks defines an undercut for the object to be formed, is movable horizontally and vertically between a molding position and a release position, and is biased towards the molding position.

This summary section is not intended to give a full description of the apparatuses and method disclosed herein. A detailed description follows.

BRIEF DESCRIPTION OF THE FIGURES

In the drawings, like reference characters generally refer to the same parts throughout the different views. Also, the drawings are not necessarily to scale, emphasis instead generally being placed upon illustrating the principles of the present disclosure.

FIG. 2 is a top perspective view of a retaining key in accordance with one embodiment of the present disclosure.

FIG. 3 is a bottom perspective view of the retaining key of FIG. 2.

FIG. 4 is a top perspective view of a key support in accordance with one embodiment of the present disclosure.

FIG. 5 is a bottom perspective view of the key support of FIG. 4.

FIG. 12A is a top view of an embodiment of a retaining key with retaining ears as the released locking portion. FIG. 12B is a side view of an embodiment of a retaining key with a wedge as the released locking portion. FIG. 12C is a top view of an embodiment of a depression void of a key support with indentions as the released locking portion.

DETAILED DESCRIPTION

Figure 1:
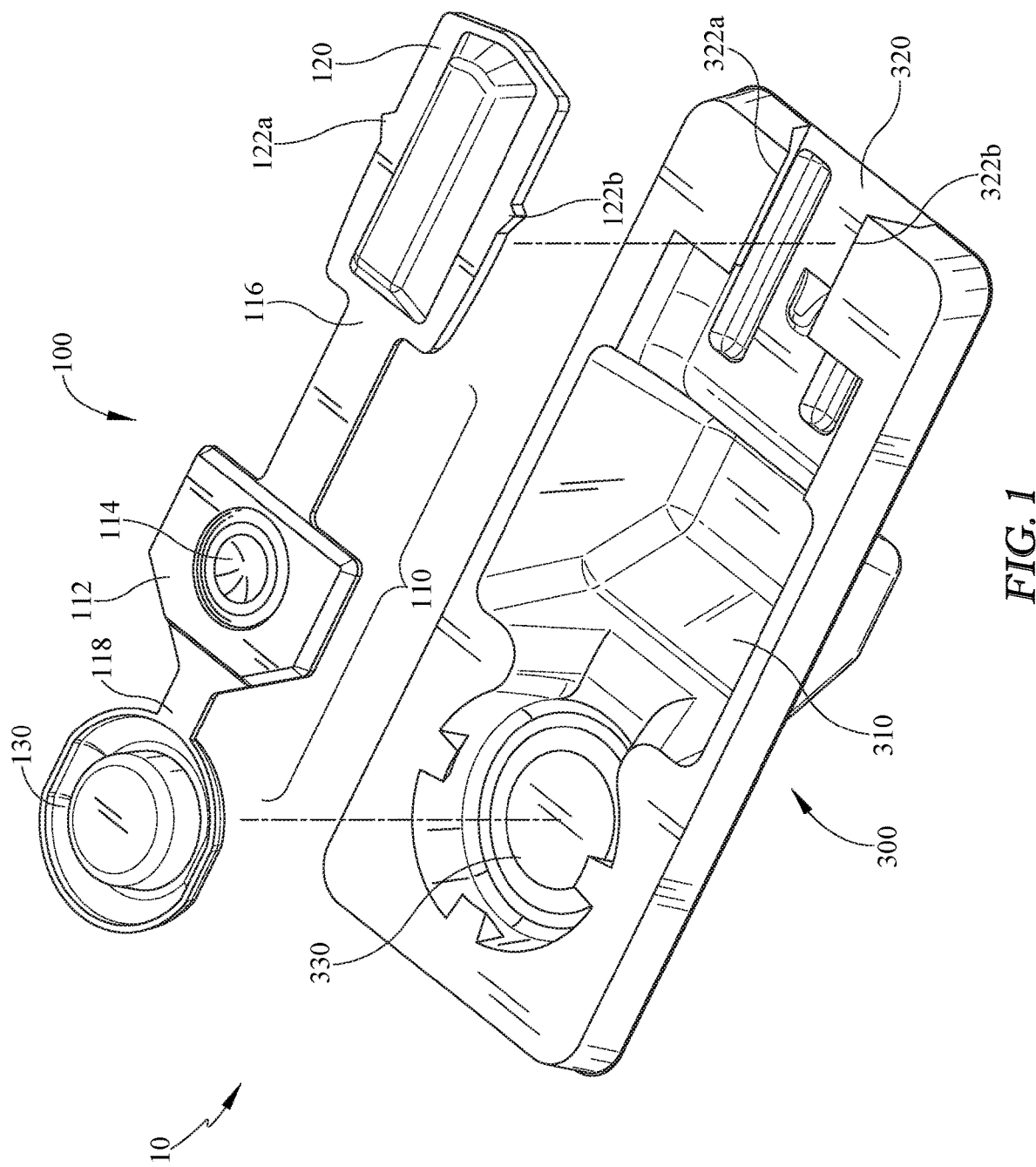
FIG. 1 is a perspective view of one embodiment of a key retention system, including a key support with a retaining key in an anchored position exploded away from the key support.

FIG. 1 illustrates an embodiment of a key retention system 10 described herein with a key support 300 and a retaining key 100 for use in containing and releasing a product from a container body. In some embodiments, the key retention system is incorporated into a container body for holding a product (see FIG. 6) and functions to retain the product in the container body until such a time when a user desires to remove the product. The retaining key 100 is movable between locked and released configurations within the key support 300. When in a locked configuration the retaining key 100 retains a portion of a product that is supported in two-dimensions by the container body; and, while in a released configuration, the retaining key retracts to facilitate the removal of the product from the container body. FIG. 1 illustrates the key retention system with the retaining key 100 in an anchored position exploded away from the key support 300.

FIGS. 2 and 3 illustrate an example embodiment of a retaining key 100 used in packaging a product, and constructed in accordance with the principles herein. The retaining key 100 described herein is movable between locked and released configurations within a key support 300 (illustrated in FIGS. 3 and 4). The retaining key 100 includes a deformable portion 110 that may extend between a tab portion 120 and an anchor portion 130. In some embodiments, the deformable portion 110 may be constructed in the form of a thin, flexible, plastic strip, but this is not to be understood as limiting, as the deformable portion 110, as the name suggests, may be constructed of any material capable of being deformed when pressure is applied. The deformable portion 110 may further contain a push target 112, which may be positioned along the length of the deformable portion 110. In some embodiments, this push target may further comprise a circular button 114, in order that it may be more easily activated by a user's finger. In other embodiments, the push target may correspond to shape of an instrument, tool, or the like that may be used to activate the push target.

A tab portion 120 may be positioned proximate a first end 116 of the deformable portion 110 of the retaining key 100, and may contain a first end 124 and a second end 126. When in an anchored position, the tab portion 120 of the retaining key 100 retains a portion of a product. In some embodiments, the tab portion contains a raised portion 128 in the center. In some embodiments, this raised portion 128 may facilitate a user in transitioning the retaining key 100 from a loading position to a locked position (described in detail below). In some embodiments, the retaining tab may further comprise a released locking portion, for example one or more retaining ears 122a, 122b, as illustrated in FIGS. 2 and 3. Other embodiments of a released locking portion are discussed below and illustrated in FIG. 12A-C. In embodiments utilizing one or more retaining ears 122a, 122b, they may be positioned in between the first end 124 and the end 126 of the retaining tab 120 and the first end 116 of the deformable portion 110. In other embodiments, the retaining ears may be attached to, or a part of, the deformable portion. Retaining ears 122a, 122b may function to maintain the retaining key 100 in a released position once released; in other words, the retaining ears 122a, 122b may function to maintain connectivity between the retaining key 100 and the support for the retaining key (not illustrated in FIGS. 2 and 3). While retaining ears 122a, 122b are illustrated in FIGS. 2 and 3, this is not intended to be limiting, as other embodiments of portions that maintain the retaining key in a released position may be used, for example see FIG. 12A-C.

In some embodiments, the tab portion of the retaining key 100 may be about ⅜ inches in length. However, this is not to be understood as limiting, as the length of the tab portion may vary depending on the size of the product to be contained, the number of retaining keys utilized to contain the product within the container body, or the like.

An anchor portion 130 may be positioned proximate a second end 118 of the deformable portion 110 of the retaining key 100. In some embodiments, as illustrated in FIGS. 2 and 3 the anchor portion 130 may be substantially circular or ovoid in shape. In some embodiments, the anchor portion 130 may be recessed inward with a raised center portion (as illustrated in FIG. 2). In other embodiments, the anchored portion 130 may be wholly recessed inward. In still other embodiments, the anchor portion 130 may be raised and contain one or more recessed notches, that may facilitate moving the retaining key in the key support from a loading position into a locked position. In some embodiments, this movement from a loading position to a locked position is achieved by sliding the retaining key.

Although illustrated, and described as, three distinct portions (the deformable portion, the tab portion, and the anchor portion) this is not to be understood as limiting. In some embodiments, the retaining key may contain only an anchor portion and a tab portion, and may be slidable, rotatable, or otherwise movable between locked and released positions to respectively retain and permit access to, a product supported within a container.

FIGS. 4 and 5 illustrate an example embodiment of a key support 300 for receiving a retaining key and packaging a product, including a depression void 310, a tab void 320, and an anchor retainer 330. The depression void 310 may be configured to receive the deformable portion 110 of the retaining key 100 when the retaining key 100 is in a released configuration (see FIG. 9). As such, in some embodiments, the depression void 310 may be deeper (e.g. extending further in a direction generally transverse to a plane of the retaining key) than the tab void 320 or the anchor retainer 330. In other embodiments, the depression void 310 may be generally cuboidal in shape; however, this is not to be understood as limiting as the depression void may be any shape capable of receiving the deformable portion. In other embodiments, the depression void may be cylindrical in shape, spherical in shape, or the like.

The tab void 320 may be configured to receive the tab portion 120 of the retaining key 100. The tab void may further comprise a narrow channel 322 constructed of a tapered wall 324a, 324b on each side of the channel 322 for receiving the tab portion 120 of the retaining key 100. In such embodiments, the tapered walls 324a, 324b are constructed at an angle such that the channel is narrower at the top of the key support 300 and wider at the bottom of the key support 300. This difference in width of the channel 322 due to the tapered walls 324a, 324b may allow the tab portion 120 of the retaining key 100 to be restricted from movement in directions other than generally along a longitudinal axis of the retaining key by the tab void 320 of the key support 300. In some embodiments, the tab void may further contain a wider portion 326 proximate the channel 322, for use in receiving the push target 112 when the retaining key is being loaded into the key support. As will become more apparent below, tapered walls 324a, 324b are separated by a gap 328 that provides sufficient spacing there between to enable a length of deformable portion 110 to fit between the tapered walls when loading retaining key 100 into key support 300. In other embodiments, however, no such spacing may be provided, or alternatively, tapered walls 324a, 324b may join together such that the gap 328 is omitted and the channel 322 is open only on opposing ends, e.g., where retaining key 100 is sized and configured to enable tab portion 120 to be inserted into one end of channel 322 when installing retaining key 100 in key support 300.

The anchor retainer 330 is configured to retain the anchor portion 130 of a retaining key 100. In some embodiments, the anchor retainer 330 may be a void, for example a circular void. In some embodiments, the anchor retainer may further comprise one or more tapered tabs (332a, 332b, 332c) positioned at the top of the anchor retainer and extending slightly over the void. These tapered tabs may be constructed at an angle such that the tabs taper inward becoming aligned with remainder of the anchor retainer. These tapered tabs may allow the anchor portion of the retaining key to be held vertically in place (i.e. be anchored) by the anchor retainer of the key support. In other embodiments, the anchor retainer 330 may be in the form a post to which the anchor portion 130 of the retaining key 100 may permanently or semi-permanently affix; additionally, or alternatively, the anchor portion 130 of the retaining key 100 may snap onto, or couple with, an anchor retainer 330 that is in the form of a post. Other manners of permanently or temporarily securing anchor portion 130 to key support 300 will be appreciated by those of ordinary skill having the benefit of the instant disclosure.

In some embodiments, the key support 300 may be substantially rectangular in shape. In other embodiments, the key support 300 may be integrally-formed (e.g. molded together) with the container body that supports or holds the product; alternatively, the key support 300 may be separately constructed, and affixed to the container body.

Figure 6:
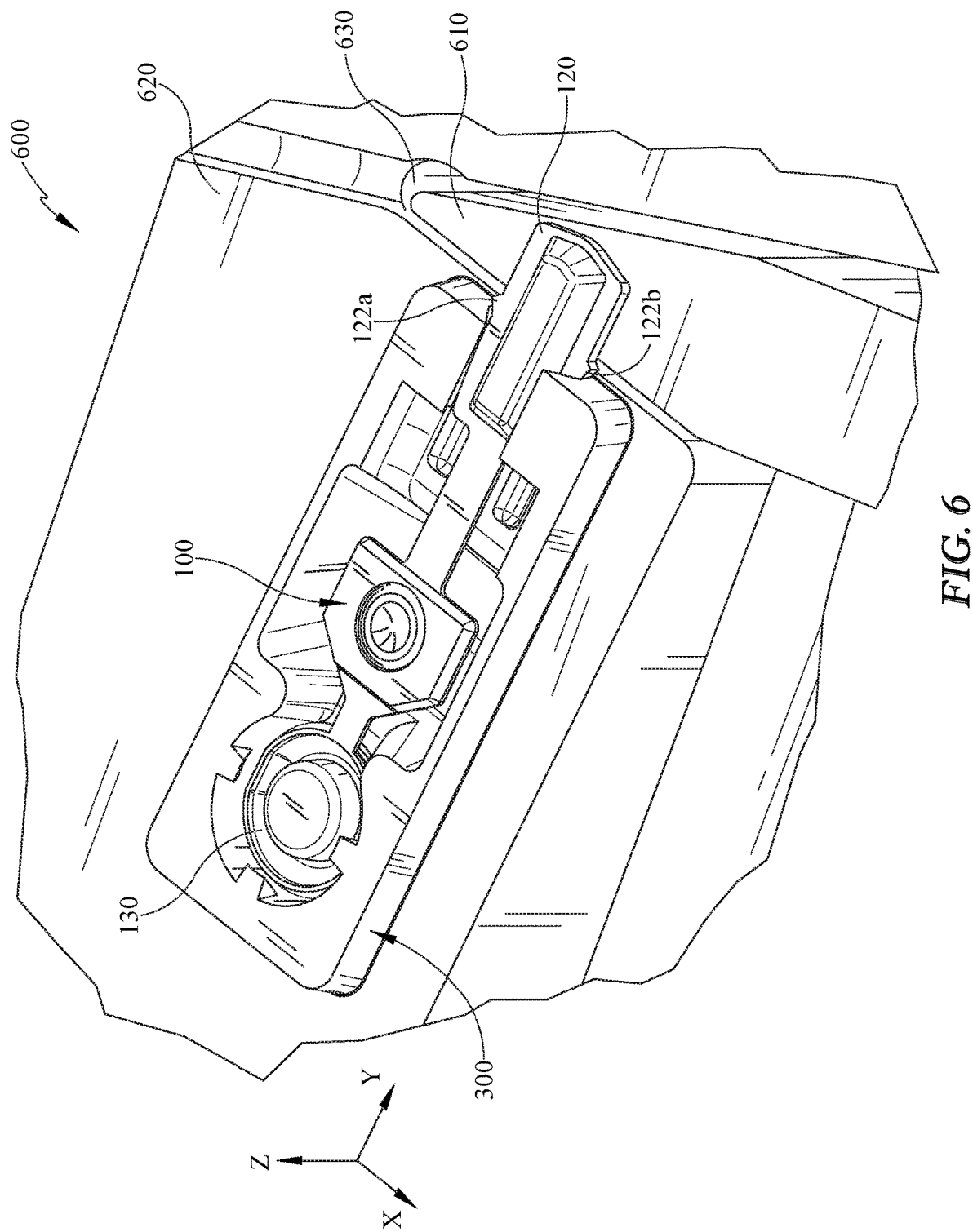
FIG. 6 is a perspective view of one embodiment of a package for a product, including a key support, a retaining key for retaining a portion of a product in the container, and a partial view of a container supporting a product.

FIG. 6 illustrates an embodiment of a package 600, including a key support 300 and a retaining key 100 for retaining a portion of a product 610 in a container body 620. In some embodiments, the product to be contained may be a medical device, instrument or component. In other embodiments, the product to be contained may be a consumer product, such as a children's toy, a household good, tool, or the like. However, this is not to be understood to be limiting, as the retaining key and key support may be used as part of a package for an innumerable variety of products, components, devices, or the like. The container body 620 may support a product 610 in two dimensions X, Y in order to minimize movement of the product in the container body. Further, the container body 620 may support the product 610 in one direction of a third dimension Z, only leaving one direction of the third dimension Z unsupported by the container body 620 (i.e. the opening of the container body 620). Dimension X, Y, and Z do not imply any particular physical orientation, and are provided for illustrative purposes only. The retaining key 100, when in an anchored position as illustrated in FIG. 6, provides this missing restraint for the product 610, restricting movement, and retaining the product 610 in the container body 620. In some embodiments, for example, a container body 620 may be configured as a tray with one or more recesses (e.g., recess 630) that generally conform to the shape of a product, and tab portion 120 of retaining key 100 may extend over one of these recesses to restrict removal of the product from the container body.

In some embodiments, the container body 620 is constructed of plastic, e.g., as may be formed via thermoforming or injection molding. In other embodiments, the container body 620 is constructed of metal, paper, or any other suitable material or combination of materials as is generally known in the art.

In some embodiments, a package for a product may include a thermoformed container body, a key support, and a retaining key for retaining a portion of a product in the thermoformed container body. In such embodiments, the key support may include a tab void and an anchor retainer. In some embodiments, the key support and container body are integrally-formed. The tab void may partially support a tab portion of the retaining key, while the anchor retainer void may support an anchor portion of the retaining key. The tab void and anchor retainer may support the retaining key and allow the retaining key to slide between a locked configuration and a released configuration. In the locked configuration the retaining key retains a portion of the product within the container body and in the released configuration the retaining key retracts to facilitate removal of the product from the container body.

Although any suitable method may be used in forming the container body 620 and key support 300, particular advantage may be achieved when the container body 620 and key support 300 are integrally-formed via a molding process. In some embodiments, this molding may be achieved through an injection molding process; in other embodiments, the molding may be achieved through a thermoforming process. In such embodiments, the key support 300 may be molded or formed as an integral part of the container body 620 from a mold during the molding or forming of the container body 620 itself. In other embodiments, the key support 300 may be separately constructed, but either permanently or removably affixed to the container body 620 that holds the product 610.

Figure 13A:
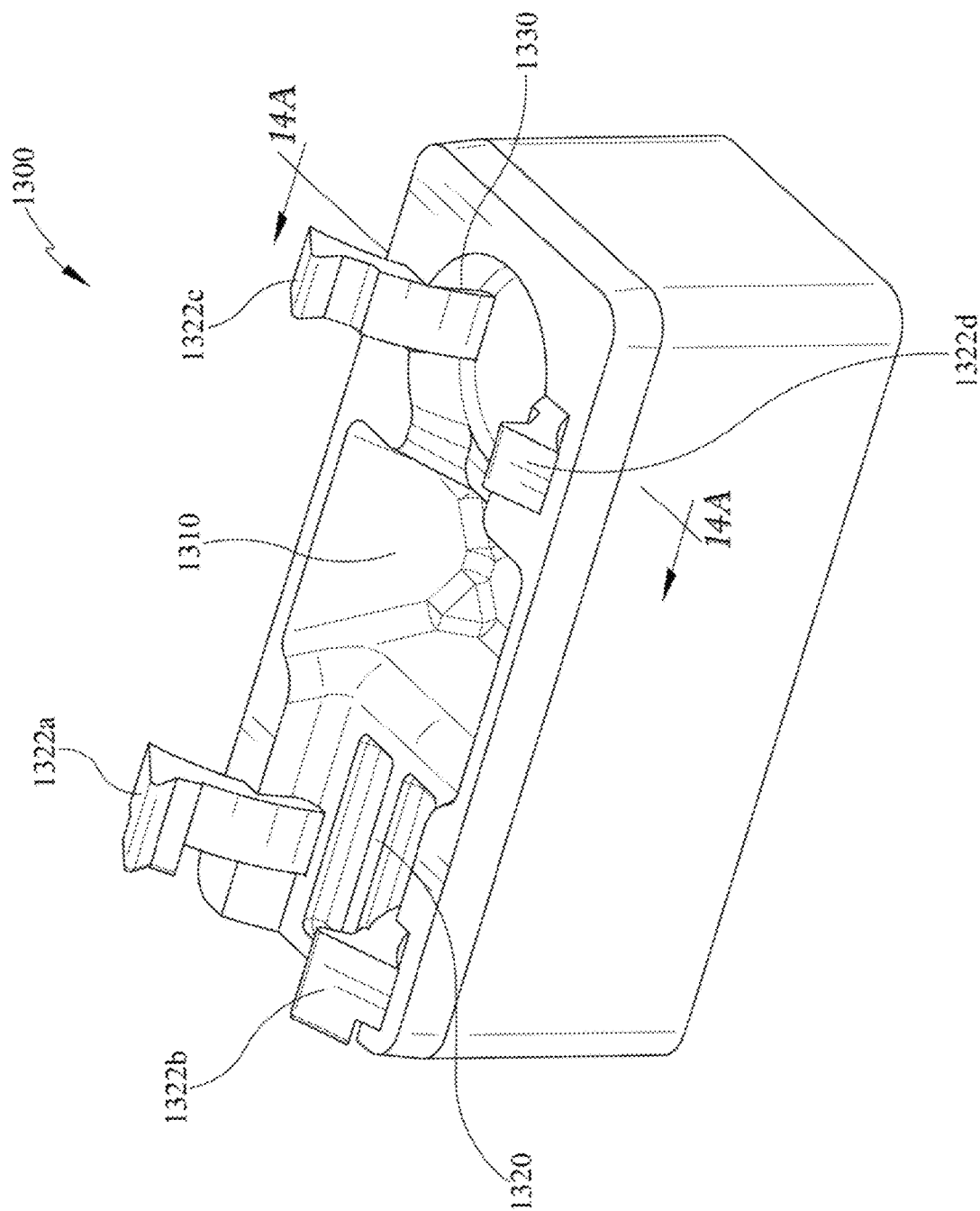
FIG. 13A is a perspective view of an embodiment of a mold for a key support in a released position.
Figure 13B:
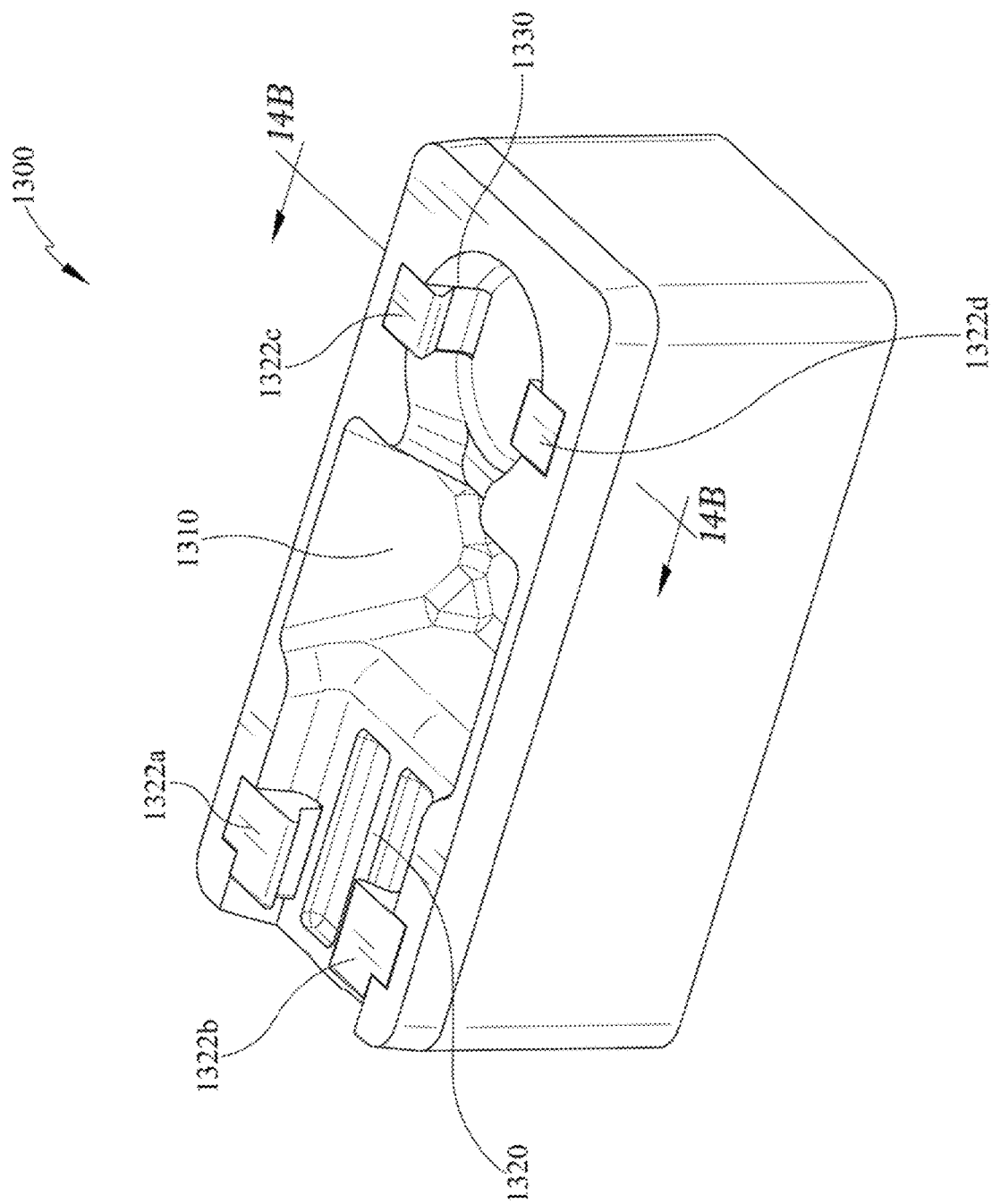
FIG. 13B is a perspective view of the mold for a key support of FIG. 13A in a molding position.
Figure 14A:
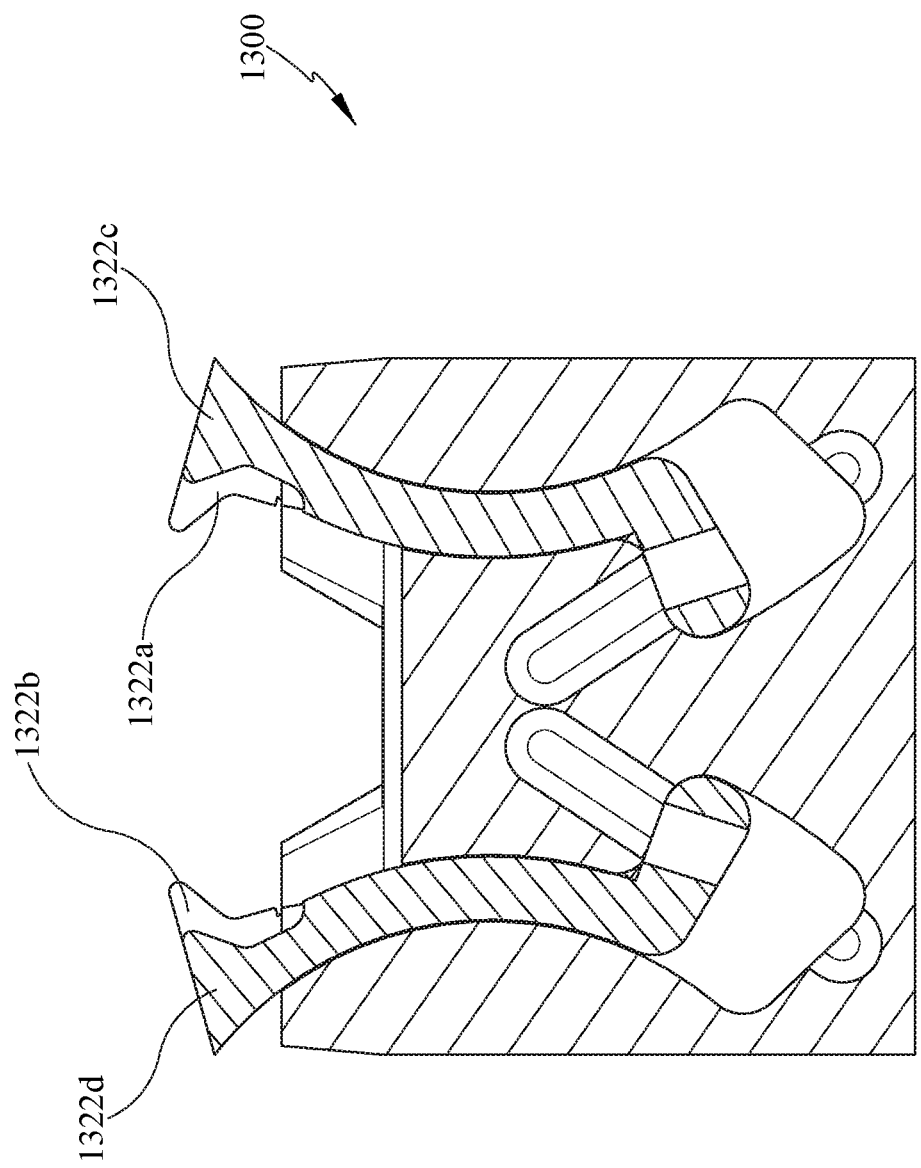
FIG. 14A is a cross-section along the line 14A-14A of FIG. 13A.
Figure 14B:
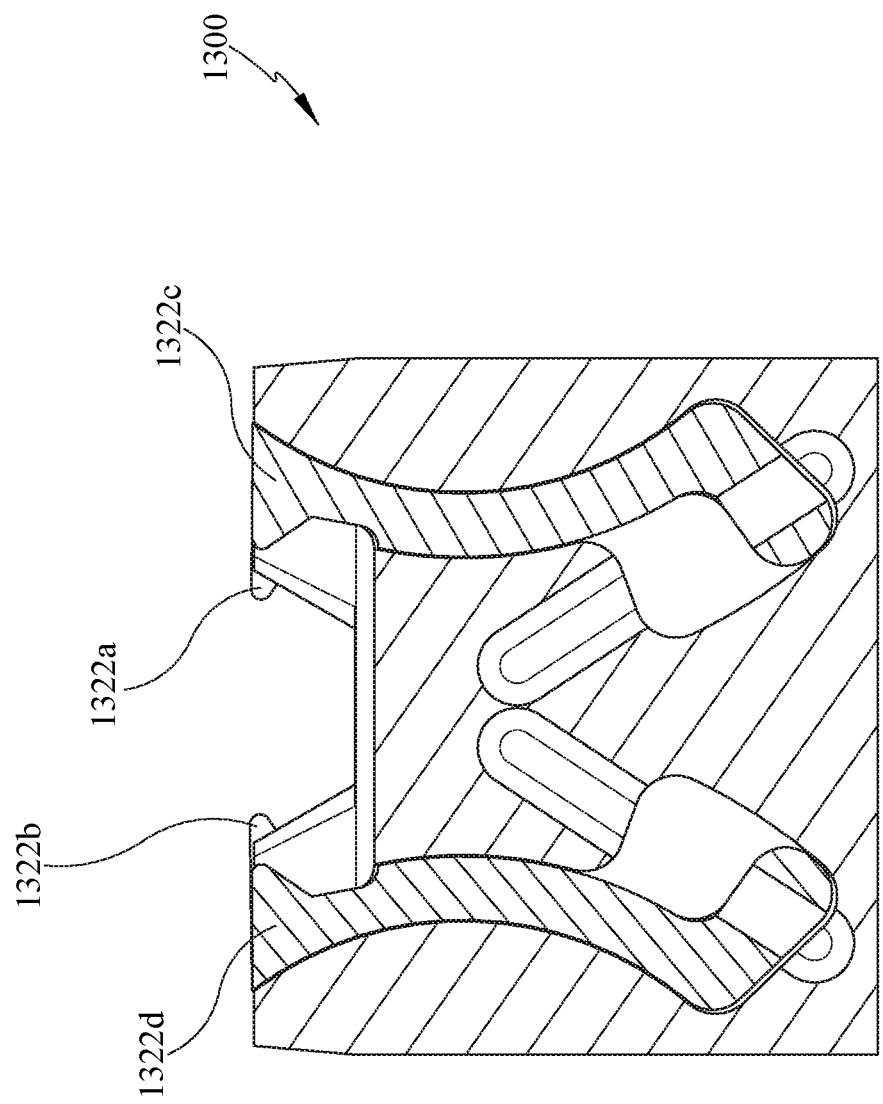
FIG. 14B is a cross-section along the line 14B-14B of FIG. 13B.

An exemplary embodiment of a mold 1300 for a key support that may be utilized in, for example, a thermoforming process, is illustrated in FIGS. 13A-B and FIGS. 14A-B. FIG. 13A illustrates the exemplary embodiment in a released position, after the molding is complete; while FIG. 13B illustrates the exemplary mold in a molding position. FIG. 14A illustrates a cross-section of FIG. 13A along line 14A-14A; while FIG. 14B illustrates a cross-section of FIG. 13B along line 14B-14B. In some embodiments, the mold may be substantially rectangular in shape so as to minimize excess waste, but is not to be understood as so limited. The mold, in order to form the key support, contains a depression void mold portion 1310, a tab void mold portion 1320, and an anchor retainer mold portion 1330. The tab void mold portion 1310 may further comprise two channel bodies 1322*a*, 1322*b*, which form the tapered walls of the channel of the key support. In some embodiments these channel bodies 1322*a*, 1322*b* may be articulating, moving between a released position, as illustrated in FIGS. 13A and 14A, and a molding position, as illustrated in FIGS. 13B and 14B. For example, it may be desirable to use such bodies when the mold is used in conjunction with a thermoforming process. In particular, some roll-fed in-line thermoforming processes may be limited in terms of the amount of undercut that may be formed in a molded container. For example, it has been found that for some roll-fed in-line thermoforming processes, e.g., those which cycle about 5 to about 40 cycles or more per minute, undercuts greater about 0.040" may cause molded parts to stick in a mold and/or may cause damage to the parts or the tooling itself when removing the molded parts from the mold. Further, such undercuts may need to be designed with a radius or angled face in order to reduce the holding force of the mold, as the more horizontal the undercut, generally the larger the holding force will be, thus making the part more likely to stick or become distorted when being removed from the mold.

It may be desirable in some embodiments for key support 300 (as illustrated in FIGS. 4 and 5) to include undercuts sized in excess of 0.060, e.g., in order to form tapering tabs 322 *a*-322 *c* and tapered walls 324 *a*, 324 *b*. Thus, in some embodiments, one or more articulating locks 1322 *a*, 1322 *b*, 1322 *c*, 1322 *d* may be incorporated into 1300, and may be spring loaded (not illustrated in FIGS. 13A-B and 14A-B) or otherwise biased toward a molding position. It should also be noted that articulating locks 1322 *a* and 1322 *b* implement the aforementioned channel bodies in tab void mold portion 1310. These articulating locks may move horizontally and vertically from a molding position to a release position when the mold and product (e.g., the key support) are separated, enabling the thermoforming of a key support 300 with a more substantial undercut in a thermoforming process. The curved nature of the articulating locks, allows them to move along an accurate path between released and molding positions. In some embodiments such articulating locks may slide from a molding position to a release position; while in other embodiments, the articulating locks may pivot from a molding position to a release position. As illustrated in FIGS. 13A-B and 14A-B, the articulating locks 1322 *a*, 1322 *b*, 1322 *c*, 1322 *d* may define an undercut for the object to be formed (e.g. the key support) and may move from a molding position to a release position.

A product may be retained within a container body utilizing a retaining key and key support through a variety of methods. An exemplary method in accordance with the principles herein includes the steps of loading a product into a container body so that the product is held in place in at least two dimensions by the container body, inserting a retaining key into a key support, such that the tab portion of the retaining key is extended over the product in a loading position, and locking the retaining key into an anchored position.

Figure 7:
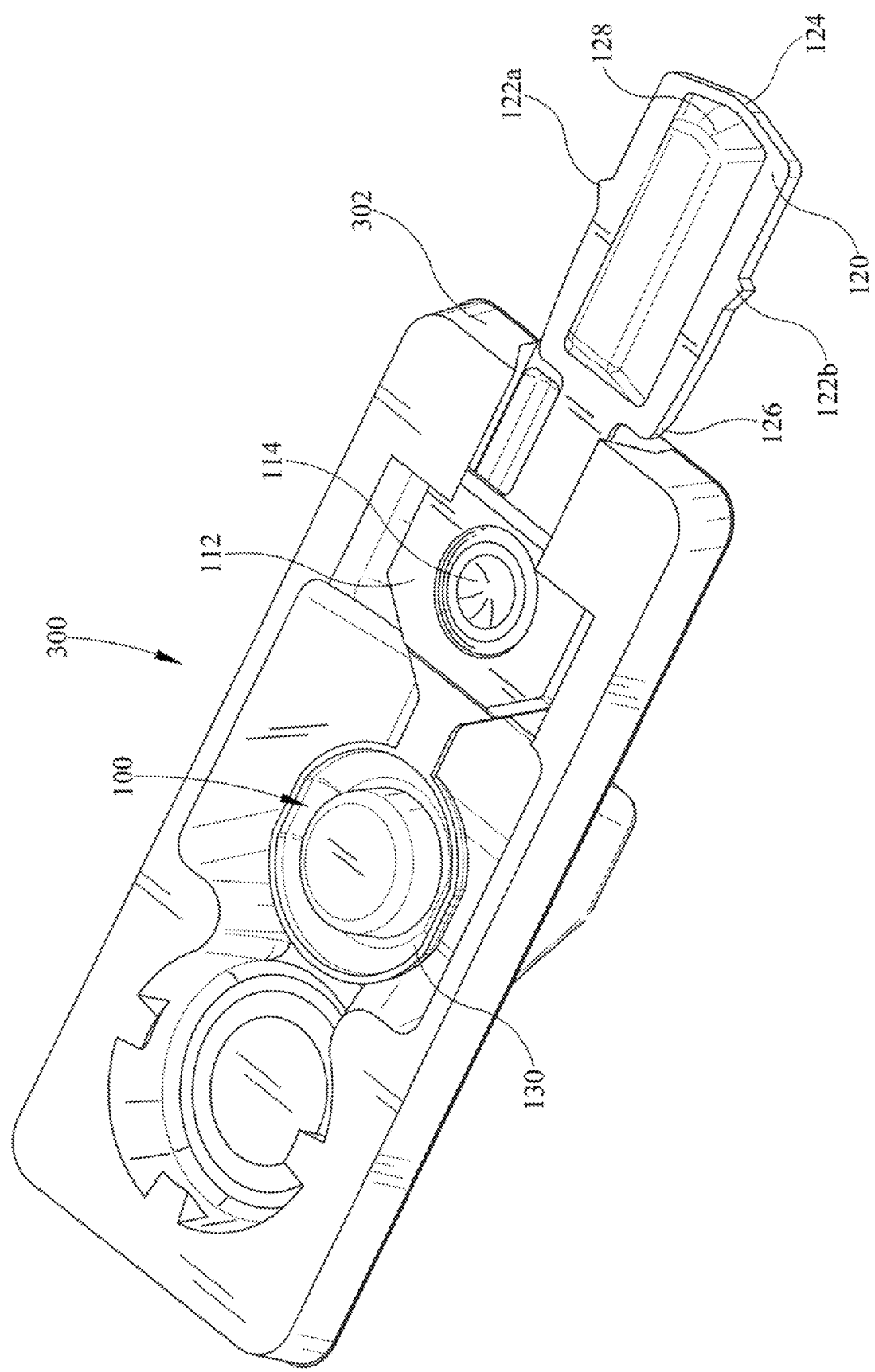
FIG. 7 is a perspective view of one embodiment of a retaining key within a key support in a loading position.

FIG. 7 illustrates an embodiment of a retaining key 100 in a key support 300 in a loading position. In the illustrated embodiment, the retaining key 100 is inserted into the key support 300 such that the narrow length of deformable portion 110 fits through gap 328 and with the tab portion 120 of the retaining key 100 hyperextended over the product to be contained (not illustrated in FIG. 7). In some embodiments, the tab portion 120 of the retaining key 100 is fully extended over the product, such that the second end 126 of the tab portion 120 is proximate a first end of the key support 302 and the first end 124 of the tab portion 120 positioned over the product. In some embodiments, the tab portion 120 may hover over the product without making contact with the product itself; while in other embodiments, the tab portion 120 may come into contact with the product and/or the container body. In the illustrated embodiment of the loading position, the push target 112 of the deformable portion 110 may also be located within the wider portion 326 of the tab void 320; while, the anchor portion 130 may be located over the depression void 310.

Figure 8:
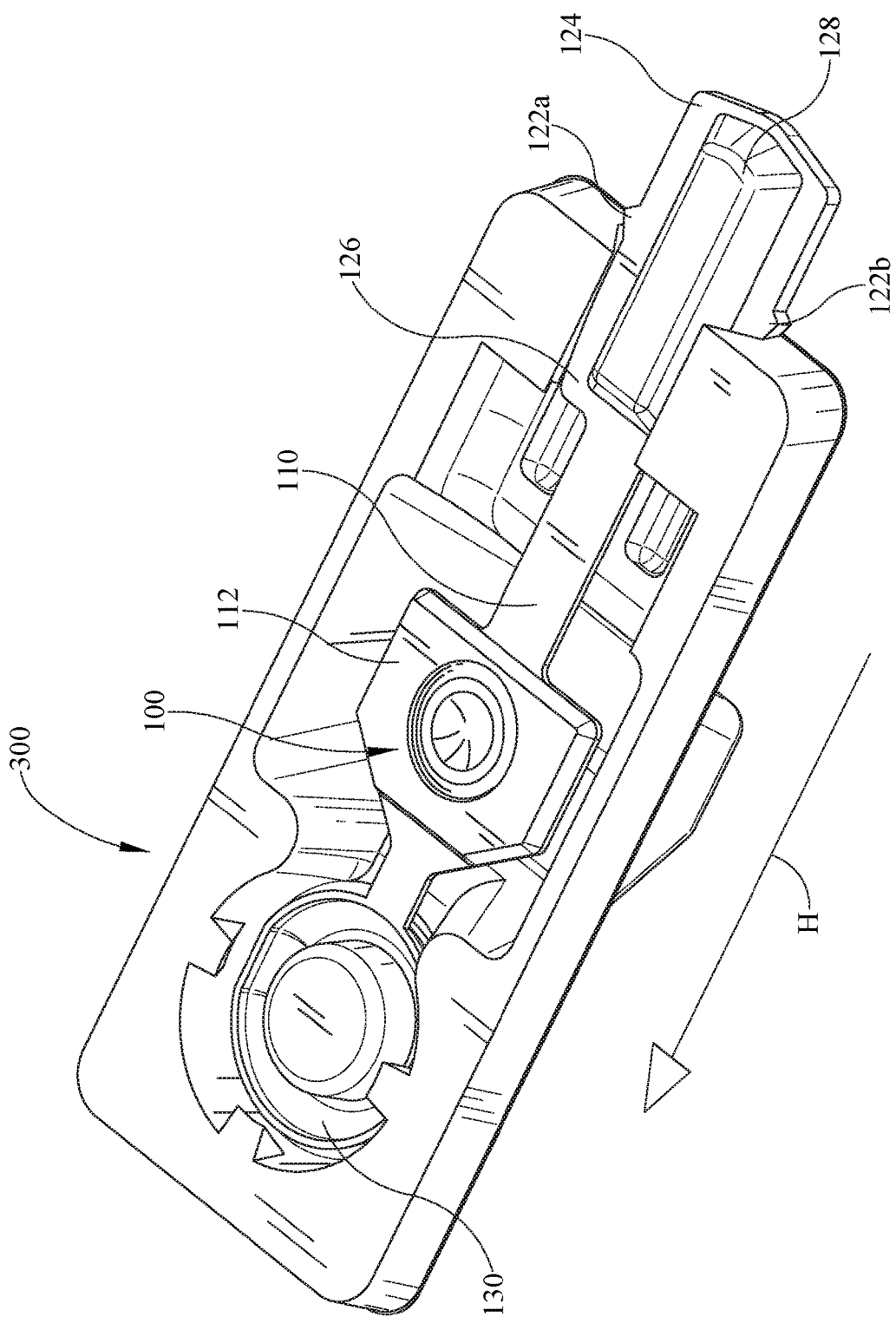
FIG. 8 is a perspective view of one embodiment of a retaining key within a key support in an anchored position.

FIG. 8 illustrates an embodiment of a retaining key 100 in a key support 300 in a locked position. In the illustrated embodiment, the retaining key 100 may be slid along a longitudinal axis H from a loading position (illustrated in FIG. 7 and described above) to a locked position, such that the second end 126 of the tab portion 120 may be contained within the tab void 320. In some embodiments the raised portion 128 of the tab portion 120 may act as a grip and facilitate a user in sliding the tab portion 120 of through the channel 322 of the retaining key 100. The channel 322, due to its tapered walls 324a, 324b (see FIGS. 4-5) may prevent the tab portion 120 from lifting up and inadvertently being removed from the key support 100. In the illustrated embodiment of the locked position, the tab portion 120 of the retaining key 100 may be at least partially extended over a product (not illustrated in FIG. 8) so that the product is retained in the container. In such an embodiment, the deformable portion 110 at least partially extends over the depression void 310. In embodiments with a push target 112, such as illustrated in FIG. 8, the push target 112 may be located approximately centrally over the depression void 310. In the illustrated embodiment of the locked position the anchor portion 130 is received in the anchor retainer 330. In other embodiments, one or more tapered tabs 332a, 332b, 332c may be positioned at the top of the anchor retainer 330, extend slightly over the void, and be constructed at an angle such that the tabs 332a, 332b, 332c taper inward becoming aligned with remainder of the anchor retainer 330. These tapered tabs 332a, 332b, 332c allow the anchor portion 130 of the retaining key 100 to be held vertically in place (anchored) by the anchor retainer 330 of the key support 300. Movement of retaining key 100 from the loading position to the locked position may therefore be accomplished in the illustrated embodiment through a combination of movement generally along axis H to position anchor portion 130 over anchor retainer 330, and then depression of anchor portion 130 into anchor retainer 330 such that the anchor portion is captured by tabs 332a, 332b, and 332c.

Just as a product may be retained within a container body utilizing a retaining key and key support through a variety of methods, so may a product be released from containment through a variety of methods. An exemplary method in accordance with the principles herein includes activating a movable portion of the retaining key and removing the product from the container body. In some embodiments, the movable portion may be a deformable portion; while in other embodiments, the movable portion may be a rotating piece.

Figure 9:
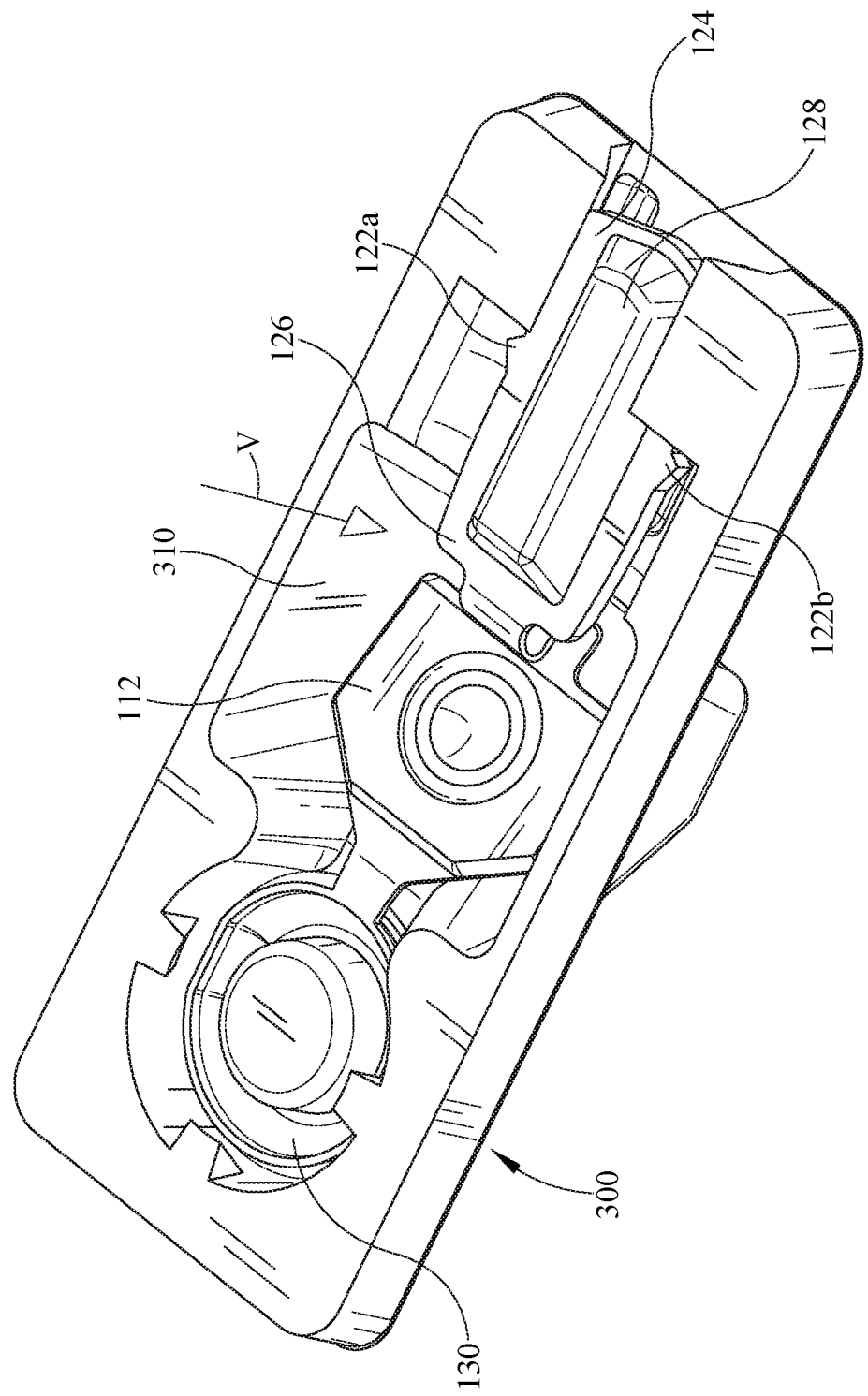
FIG. 9 is a perspective view of one embodiment of a retaining key within a key support in a released position.

FIG. 9 illustrates an embodiment of a retaining key 100 in a key support 300 in a released position. In the illustrated embodiment, the push target 112 is depressed along a vertical axis V. This depression results in at least part of the deformable portion 110 flexing, or collapsing, into the depression void 310. In some embodiments, the push target 112 may be depressed (or activated) by a user's finger. In other embodiments, the push target 112 may be depressed (or activated) by an instrument, tool, or the like. In some embodiments there may not be a push target 112 at all, in such embodiments a portion of the deformable portion 110 located over the depression void 310 may be depressed, by any means (e.g. a user's finger, tool, instrument, or the like), resulting in at least part of the deformable portion 110 flexing or collapsing into the depression void 310. The flexing, or collapse of, the deformable portion 110 into the depression void 310 simultaneously causes the tab portion 120 to retract away from the product contained within the container body, thereby moving the tab portion away from a position in which it retains the product in the container body. In some embodiments, the first end 124 of the tab portion 120 retracts fully into the channel 322 of the tab void 320, although the invention is not so limited.

In some embodiments the push target 112 of the deformable portion 110, may be depressed (e.g. by a user's finger, instrument, tool, or the like) by a single handed movement of a user, which may be desirable under certain circumstances (e.g. with a medical device in a sterile environment).

A retaining key in combination with a key support, as described in various embodiments herein, work to retain a product in a container body until such a time as a user desires and activates a release mechanism (e.g. deformable portion, or rotatable cam) to allow the product to be removed. When in a released position, a retaining key may maintain its connectivity to the key support. In some embodiments, the retaining key and the key support may be permanently or semi-permanently connected. This permanent or semi-permanent connectivity may be desirable in circumstances where multiple packaging components are problematic. For example, such permanent or semi-permanent connectivity of product packaging components may be desirable where the product is a medical device or in an operating room environment where each packaging piece may need to be accounted for at the end of a procedure; in children's product packaging where small packaging pieces may pose a choking hazard; and so on.

It may also be desirable in some embodiments to configure a retaining key and key support to maintain the retaining key in the released position, i.e., to prevent the key from being moved back to the locked position from the released position. It may be particularly desirable, for example, when multiple retaining keys and key supports are used to secure one or more products into a container body, as the multiple retaining keys may be individually actuated and maintained in the released position to facilitate removal of the product(s) from the container body once all retaining keys have been actuated. Various mechanisms may be used to lock a retaining key in a released position, and in this regard, a retaining key and/or key support in some embodiments may include one or more released locking portions for locking the retaining key 100 and the key support 300 into a permanent or semi-permanent released position.

Figure 12A:
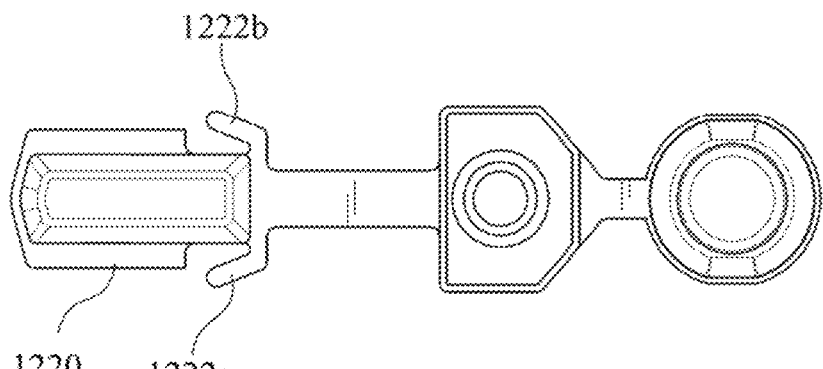
FIG. 12A-C illustrate various embodiments of released locking portions of the retaining key.
Figure 12B:
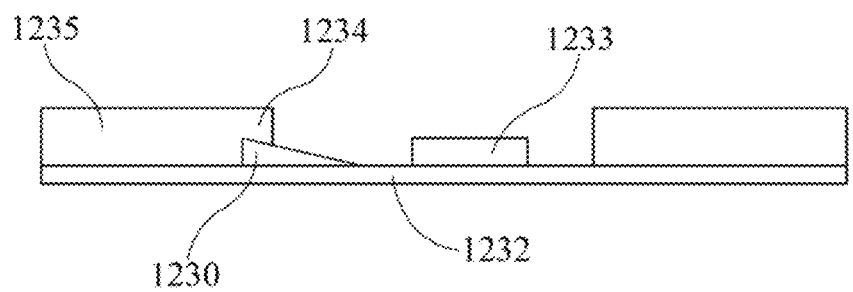
Figure 12C:
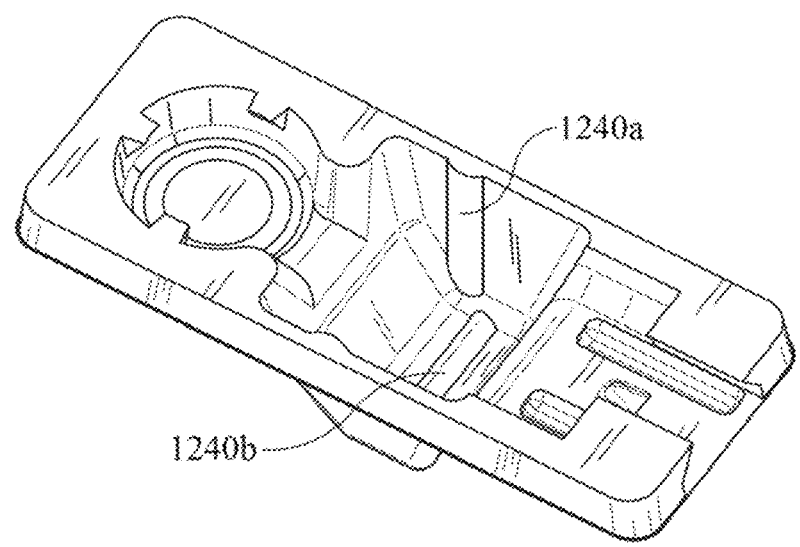

FIGS. 12A-12C, for example, illustrate three such exemplary configurations. FIG. 12A illustrates an embodiment of a released locking portion in the form of one or more retaining ear portions 1222a, 1222b (also see FIGS. 2 and 3). These one or more retaining ear portions 1222a, 1222b may be a part of the tab portion 1220; while in other embodiments, the retaining ear portions may be a part of the deformable portion. In some embodiments, the retaining ear portions 1222a, 1222b may be flexible, and may function by flexing and contacting the tab void of the key support. FIG. 12B illustrates another exemplary embodiment of a released locking portion, where the released locking portion is in the form of one or more wedge portions 1230 positioned proximate a first end 1232 of a deformable portion 1233 and a second end 1234 of a retaining tab 1235. In such embodiments, the one or more wedge portions 1230 may contact the tab void and thus prevent movement from the released position back to the locked position. FIG. 12C illustrates yet another exemplary embodiment of a released locking portion, where the release locking portion is in the form of one or more indentions 1240a, 1240b in the depression void of the key support. In such an embodiment, the deformable portion of the retaining key may be shaped to lock into the one or more indentions once depressed into the void. The preceding exemplary embodiments are not to be understood to be limiting, as those of skill in the art recognize there are a variety of mechanisms that may be used for maintaining permanent or semi-permanent connectivity between the key support and the retaining key to maintain the retaining key in the released position.

Although FIGS. 8 and 9 illustrate utilizing a sliding/depression mechanism for locking and releasing the retaining key 100, this is not to be understood as limiting. In some embodiments, the locking and releasing step may be accomplished by a rotating mechanism, such as illustrated in FIGS. 10 and 11.

Figure 10:
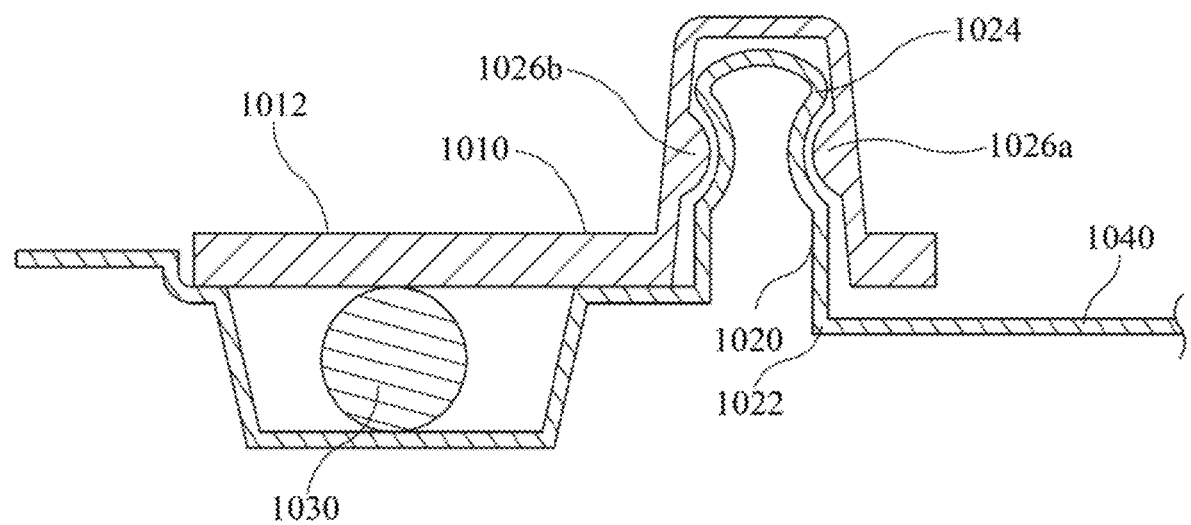
FIG. 10 is a front view of another embodiment of a package for a product, including a key support, a retaining key for retaining a portion of a product in the container, and a partial view of a container supporting a product.

FIG. 10 illustrates another embodiment of a package for a product, including a key support 1020 and a retaining key 1010 for retaining a portion of a product 1030 in a container body 1040. In the illustrated embodiment, the retaining key 1010 may rotate to facilitate the removal of the product 1030 from the container body 1040. The retaining key may include a cam portion 1014 configured as an eccentric disc located at or near a first end of a tab portion 1012. The tab portion 1012 may mechanically link to a key support 1020. In some embodiments, the key support 1020 may be in the form of a post with a first end 1022 and a second end 1024. The first end 1022 of the key support 1020 may be integrally-formed (e.g. through thermoforming, injection molding, or the like) with the container body 1030. In other embodiments, the first end 1022 of the key support 1020 may be affixed to the container body, so that it may be coupled with the retaining key 1010, allowing the retaining key 1010 to mechanically link with the key support 1020. In some embodiments, the second end 1024 of the key support 1020 may be generally rounded-off, but this should not be understood be limiting. In other embodiments, the second end 1024 of the key support 1020 may further contain one or more indentions 1026a, 1026b that may facilitate mechanical linking with the retaining key 1010. In some embodiments, the retaining key 1010 may be placed on top off the key support 1020, such that a tab portion 1012 of the retaining key 1010 is covering the product 1040 supported by the container body 1030. The retaining key 1010 may "snap" or lock onto the key support 1020 through use of the one or more indentions 1026a, 1026b.

Figure 11:
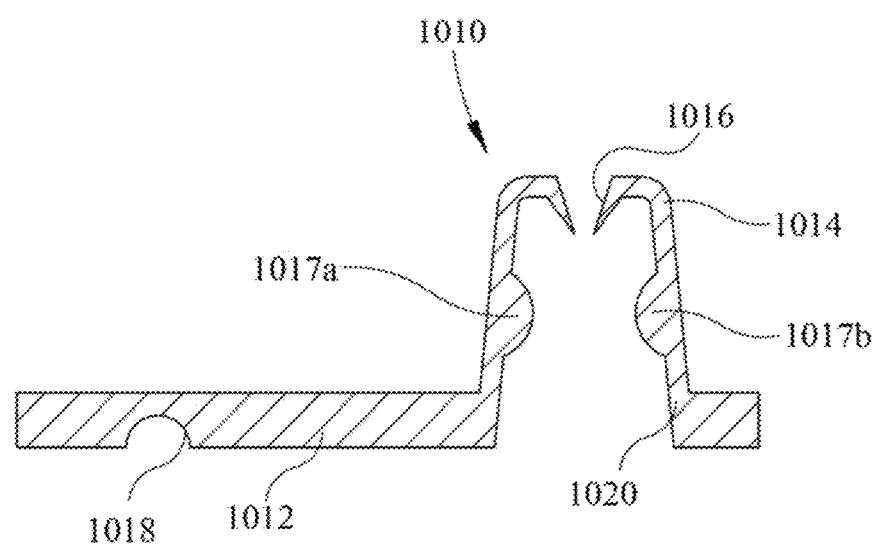
FIG. 11 is a front view of another embodiment of a retaining key.

FIG. 11 illustrates another embodiment of a retaining key 1010. In the illustrated embodiment, the retaining key 1010 contains a tab portion 1012 that may cover a product 1040 supported by a container body 1030. In some embodiments, the tab portion 1010 may hover over a product 1040 without making contact with the product 1040 itself; while in other embodiments, the tab portion 120 may come into contact with the product 1040 in the body 1030 (as illustrated in FIG. 10). In some embodiments, the tab portion 1010 may also contain a recessed portion (or an indention) 1018, which may serve as a mechanism for stopping the retaining key 1010 and locking it into a released position by coupling this recessed portion 1018 with a corresponding raised portion of the container body (not illustrated).

The cam portion 1014 of the retaining key 1010 of FIGS. 10 and 11 may be rotated in order to move the tab portion 1012 of the retaining key 1010 into a released position. The cam portion 1014 may be in the form of a hollow post, so as to envelope the key support 1020. The cam portion 1014 may contain one or more protrusions 1017a, 1017b that extend from the underside of the hollow space. These protrusions 1017a, 1017b facilitate the mechanical linking with the one or more indentions 1026a, 1026b of the key support 1010, and in some embodiments, the retaining key is "snapped" or locked onto the key support 1010 through these protrusions and indentions.

In some embodiments, a user may grip the cam portion 1014 of the retaining key 1010 and manually rotate the retaining key 1010 into a released position so that the retaining tab 1012 is no longer covering the product 1040, allowing the product to be removed from the container body 1030. In other embodiments, the cam portion 1014 may further contain a target 1016 that may receive an instrument, tool, or the like, in order to facilitate rotation of the retaining key 1010. The use of such an instrument, tool, or the like may, in some instances, be desirable when a sterile or aseptic environment is to be maintained.

While several embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The foregoing description of several embodiments of the invention has been presented for purposes of illustration. It is not intended to be exhaustive or to limit the invention to the precise steps and/or forms disclosed, and obviously many modifications and variations are possible in light of the above teaching.

We claim:

1. A package for a product, comprising:
    a container body configured to support the product and including a key support; and
    a separately-formed retaining key attached to and supported by the key support and movable between locked and released configurations, wherein in the locked configuration the retaining key retains a portion of the product when the product is supported by the container body and in the released configuration, the retaining key retracts to facilitate removal of the product from the container body when the product is supported thereby, wherein the retaining key includes a tab portion, a deformable portion and an anchor portion, and wherein:
        the deformable portion extends between the tab portion and the anchor portion and is configured to be suspended over a void defined by the key support when the retaining key is supported by the key support;
        depression of the deformable portion into the void moves the retaining key from the locked configuration to the released configuration;
        the tab portion is disposed proximate a first end of the deformable portion and is configured to retain the portion of the product when the product is supported by the container body and the retaining key is in the locked configuration; and
        the anchor portion is disposed proximate a second end of the deformable portion and is configured to attach to the key support to anchor the retaining key to the key support proximate the second end thereof.

2. The packaging of claim 1, wherein the deformable portion includes a push target for depressing the deformable portion into the void.

3. The packaging of claim 2, wherein the push target for depressing the deformable portion into the void is sized and configured to be activated by a user's finger.

4. The packaging of claim 1, wherein the key support is integrally-formed with the container body.

5. The packaging of claim 1, wherein the key support includes a channel and wherein the tab portion of the retaining key is slidably received in the channel such that the tab portion slides within the channel when the retaining key is moved from the locked configuration to the released configuration.

6. The packaging of claim 1, wherein the retaining key is inseparable from the key support.

7. The packaging of claim 1, wherein the product is a medical device.

8. A retaining key for packaging a product, comprising:
a tab portion, a deformable portion and an anchor portion;
wherein the deformable portion extends between the tab portion and the anchor portion and is configured to be suspended over a void defined by a key support in a container body that supports the product;
wherein depression of the deformable portion into the void moves the retaining key from a locked configuration to a released configuration;
wherein the tab portion is disposed proximate a first end of the deformable portion and is configured to retain a portion of the product when the product is supported by the container body and the retaining key is in the locked configuration;
wherein the anchor portion is disposed proximate a second end of the deformable portion and configured to anchor the retaining key to the key support proximate the second end thereof;
wherein the tab portion is configured to be slidably received in a channel defined by the key support when the retaining key is anchored to the key support; and
wherein the retaining key is movable between the locked and released configurations, wherein in the locked configuration the retaining key retains a portion of the product when the product is supported by the container body and in the released configuration, the retaining key retracts to facilitate removal of the product from the container body when supported thereby.

9. The retaining key of claim 8, wherein the deformable portion includes a push target for depressing the deformable portion into the void.

10. The retaining key of claim 9, wherein the push target for depressing the deformable portion into the void is sized and configured to be activated by a user's finger.

11. The retaining key of claim 8, wherein the retaining key is separately-formed from the key support and is attachable to the key support through the anchor portion.

12. The retaining key of claim 8, wherein the deformable portion is narrower than the tab portion.

13. A key support for packaging a product, comprising:
a depression void capable of receiving a deformable portion of a retaining key when the deformable portion is depressed into the depression void;
a tab void capable of at least partially receiving a tab portion of the retaining key proximate a first end of the deformable portion of the retaining key;
an anchor retainer capable of receiving an anchor portion of a retaining key proximate a second end of the deformable portion of the retaining key; and
wherein the key support supports the retaining key in a container body and allows the retaining key to move between locked and released configurations, wherein in the locked configuration the retaining key retains a portion of the product when the product is supported by the container body and in the released configuration, the retaining key retracts to facilitate removal of the product from the container body when supported thereby.

14. The key support for packaging a product of claim 13, wherein the key support is integrally-formed with the container body.

15. The key support for packaging a product of claim 13, wherein the depression void is substantially rectangular in shape.

16. The key support for packaging a product of claim 13, wherein the anchor retainer is substantially circular in shape.

17. The key support for packaging a product of claim 13, wherein the anchor retainer includes a top portion and a bottom portion, wherein the top portion includes one or more tapered tabs at an angle such that the tapered tabs taper inwardly to align with the bottom portion of the anchor retainer to hold the anchor portion in place.

18. The key support for packaging a product of claim 13, wherein the deformable portion of the retaining key is narrower in cross-section than the tab portion of the retaining key, wherein the tab void includes a channel sized and configured to receive the tab portion of the retaining key for movement along a first axis and formed from a first tapered wall and a second tapered wall, wherein the first and the second tapered walls are separated by a gap that is narrower than the tab portion of the retaining key but wider than at least a portion of the deformable portion of the retaining key to enable the at least a portion of the deformable portion of the retaining key to be inserted into the channel of the tab void when attaching the retaining key to the key support, and wherein the tab void is positioned relative to the anchor retainer such that at least a portion of the tab portion is positioned within the channel when the anchor portion of the retaining key is received by the anchor retainer of the key support.

19. A package for a product, comprising:
a thermoformed container body configured to support the product;
a tab void at least partially supporting a tab portion of a retaining key;
an anchor retainer supporting an anchor portion of the retaining key; and
wherein the tab void and anchor retainer support the retaining key and allow the retaining key to slide between locked and released configurations, wherein in the locked configuration the retaining key retains a portion of the product when the product is supported by the container body and in the released configuration, the retaining key retracts to facilitate removal of the product from the container body when supported thereby.

20. A mold for use in product packaging container, comprising:
a depression void portion capable of defining a depression void in a container body that receives a deformable portion of a retaining key when the deformable portion is depressed into the depression void;
a tab void portion capable of defining a tab void in the container body that at least partially receives a tab portion of the retaining key proximate a first end of the deformable portion of the retaining key;
an anchor retainer portion capable of defining an anchor retainer in the container body that receives an anchor portion of the retaining key proximate a second end of the deformable portion of the retaining key; and
wherein the depression void, tab void, and anchor retainer support form a key support when used into combination with a container body configured to support the product.

21. The mold of claim 20, wherein the thermoform mold is substantially rectangular in shape.

22. The mold of claim 20, wherein the depression void is substantially rectangular in shape.

23. The mold of claim 20, wherein the anchor retainer is substantially circular in shape.

24. The mold of claim 20, wherein the mold further comprises one or more articulating locks, wherein the one or more articulating locks are movable from a molding position to a release position and biased towards the molding position.

25. The mold of claim 24, wherein the one or more articulating locks move horizontally and vertically from a molding position to a release position.

* * * * *